US006100535A

United States Patent [19]
Mathies et al.

[11] Patent Number: 6,100,535
[45] Date of Patent: Aug. 8, 2000

[54] ROTARY CONFOCAL SCANNER FOR DETECTION OF CAPILLARY ARRAYS

[75] Inventors: Richard A. Mathies, Moraga; James R. Scherer, Berkeley; David Wexler, San Francisco, all of Calif.

[73] Assignee: The Regents of the University of California, Oakland, Calif.

[21] Appl. No.: 09/015,198

[22] Filed: Jan. 29, 1998

[51] Int. Cl.[7] .................................................. G01N 21/64
[52] U.S. Cl. .......................................................... 250/458.1
[58] Field of Search ........................................... 250/458.1

[56] References Cited

U.S. PATENT DOCUMENTS

| | | |
|---|---|---|
| 5,091,652 | 2/1992 | Mathies et al. . |
| 5,274,240 | 12/1993 | Mathies et al. . |
| 5,483,075 | 1/1996 | Smith et al. . |
| 5,538,613 | 7/1996 | Brumley et al. . |

OTHER PUBLICATIONS

Ansorge, William et al.; Automated DNA sequencing: ultrasensitive detection of fluorescent bands during electrophoresis, Nucleic Acids Research, *IRL Press Limited,* vol. 15, No. 11 (1987), pp. 4593–4603.

Brumbaugh, John A., et al.; Continuous, on–line DNA sequencing using oligodeoxynucleotide primers with multiple fluorophores, Genetics, *Proc. Natl. Acad. Sci.,* vol. 85 (Aug. 1988), pp. 5610–5614.

Prober, James M. et al.; A System for Rapid DNA Sequencing with Fluorescent Chain–Terminating Dideoxynucleotides, *Science,* vol. 238 (Oct. 1987), pp. 336–341.

Smith, Lloyd M., et al.; Fluorescence detection in automated DNA sequence analysis, *Nature,* vol. 321 (Jun. 1986), pp. 674–678.

Quesada, M.A., et al.; High–Sensitivity DNA Detection with a Laser–Excited Confocal Fluorescence Gel Scanner, *Bio Techniques,* vol. 10, No. 5 (1991).

Huang, Xiaohua C., et al.; Capillary Array Electrophoresis Using Laser–Excited Confocal Fluorescence Detection, *Analytical Chemistry,* vol. 64, No. 8 (Apr. 1992).

Mathies, Richard A., and Huang, Xiaohua C., Capillary array electrophoresis: an approach to high–speed, high–throughput DNA sequencing, *Nature,* vol. 359 (Sep. 1992), pp. 167–169.

Huang, Xiaohua C., et al.; DNA Sequencing Using Capillary Array Electrophoresis, *Analytical Chemistry,* vol. 64, No. 18 (Sep. 1992), pp. 2149–2154.

Mathies, Richard A., et al.; Laser–excited confocal–fluorescence gel scanner, *Rev. Sci. Instrum.* 65(4) (Apr. 1994), pp. 807–812.

Kheterpal, Indu, et al.; DNA sequencing using a four–color confocal fluorescence capillary array scanner, *Electrophoresis* 17 (1996), 1852–1859.

Woolley, Adam T., and Mathies, Richard A., Ultra–High Speed DNA Sequencing Using Capillary Array Electrophoresis Chips, *SPIE* vol. 2386 (May 1995) pp. 36–44.

Woolley, Adam T., and Mathies, Richard A., Ultra–High–Speed DNA Sequencing Using Capillary Electrophoresis Chips, *Analytical Chemistry,* vol. 67, No. 20 (Oct. 1995) pp. 3676–3680.

Woolley, Adam T., et al.; Functional Integration of PCR Amplification and Capillary Electrophoresis in a Microfabricated DNA Analysis Device, *Analytical Chemistry,* vol. 68, No. 23 (Dec. 1996), pp. 4081–4086.

Woolley, Adam T. et al.; High–Speed DNA Genotyping Using Microfabricated Capillary Array Electrophoresis Chips, *Analytical Chemistry,* vol. 69, No. 11 (Jun. 1997) pp. 2181–2186.

Koutny, Lance B., et al.; Microchip Electrophoretic Immunoassay for Serum Cortisol, *Analytical Chemistry,* vol. 68, No. 1 (Jan. 1996) pp. 18–22.

*Primary Examiner*—Constantine Hannaher
*Assistant Examiner*—Andrew Israel
*Attorney, Agent, or Firm*—Flehr Hohbach Test Albritton & Herbert LLP

[57] ABSTRACT

A confocal scanner which scans a circular path traversing capillaries in a planar array for detecting separations performed in said capillaries.

10 Claims, 6 Drawing Sheets

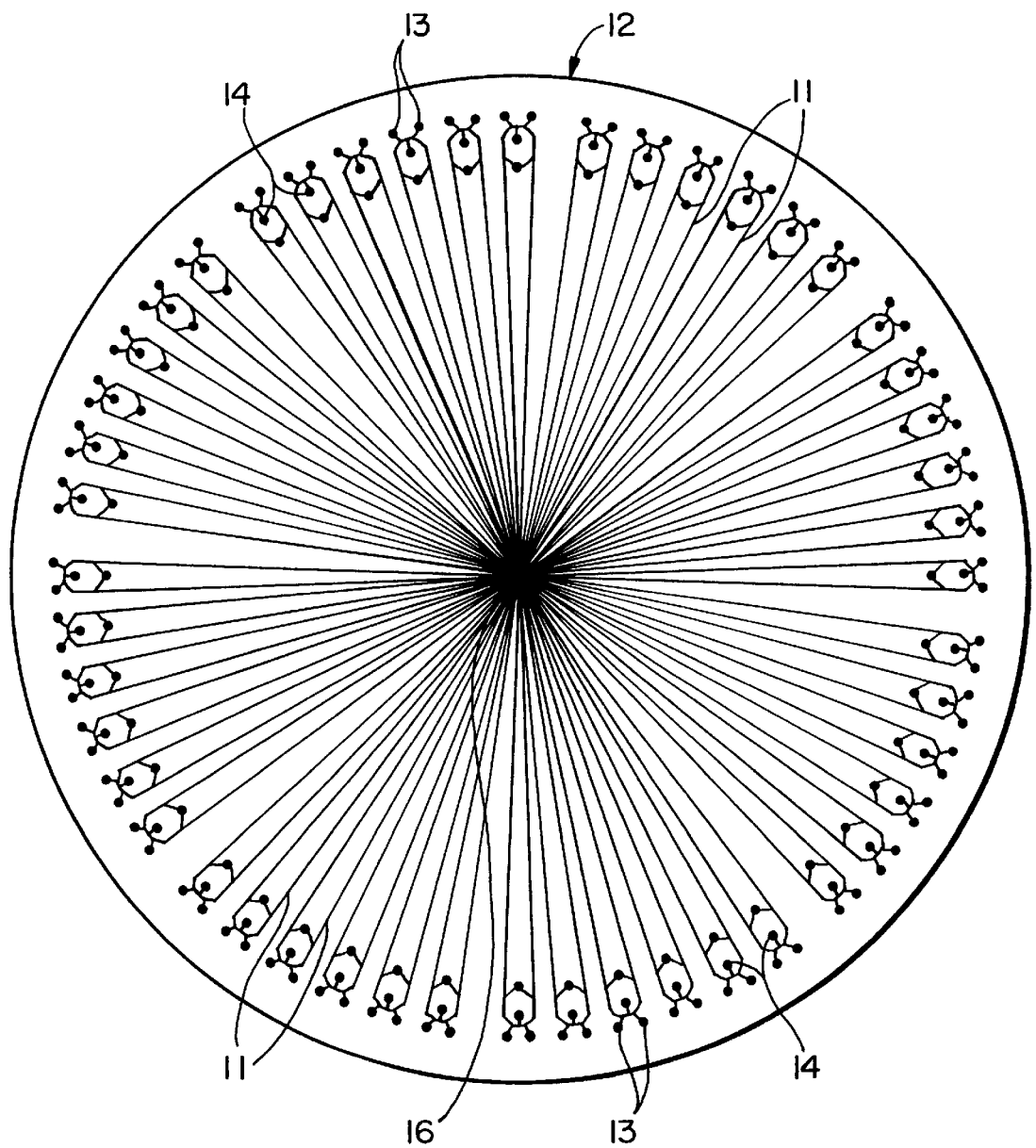
FIG_1

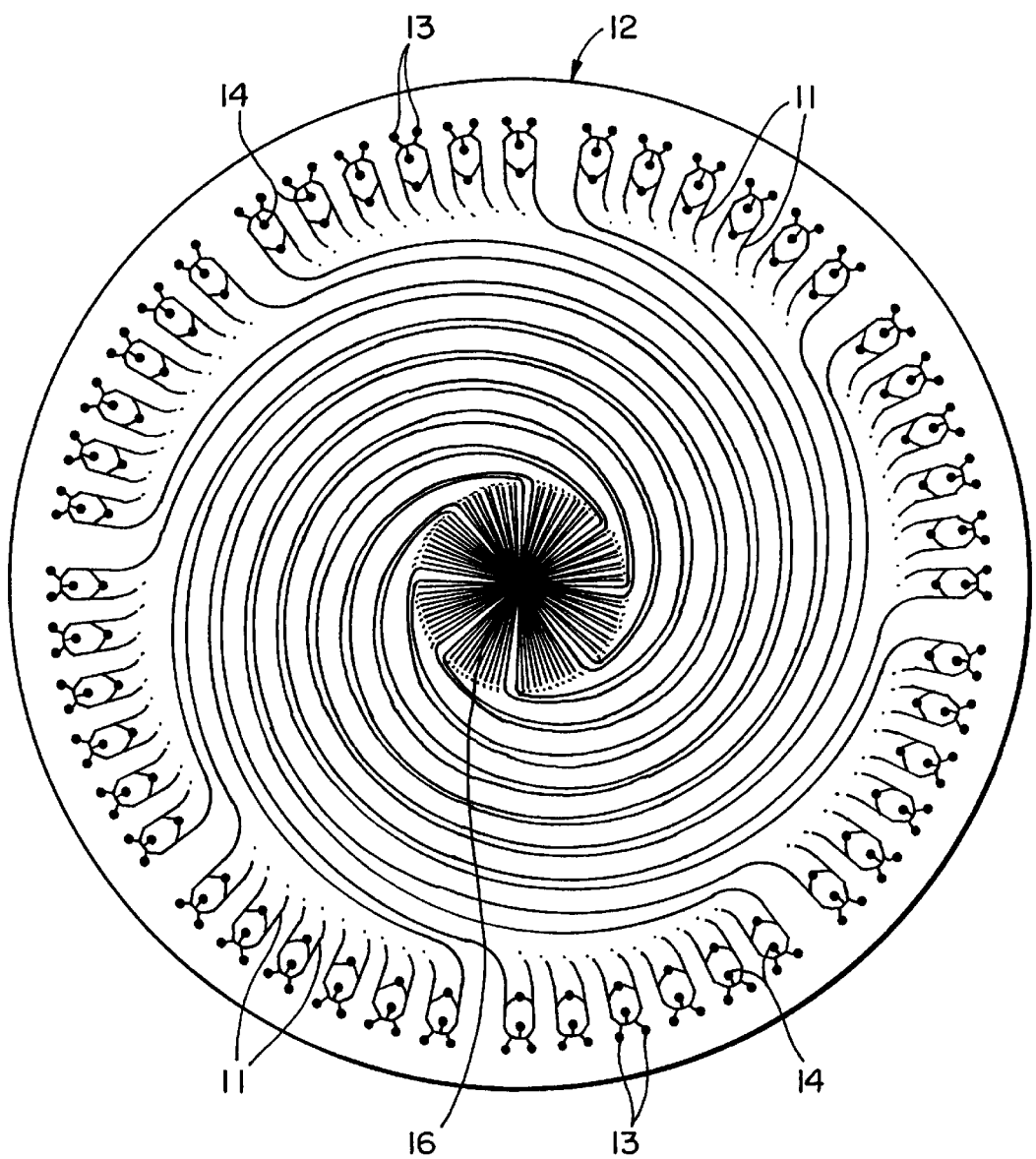
FIG_2

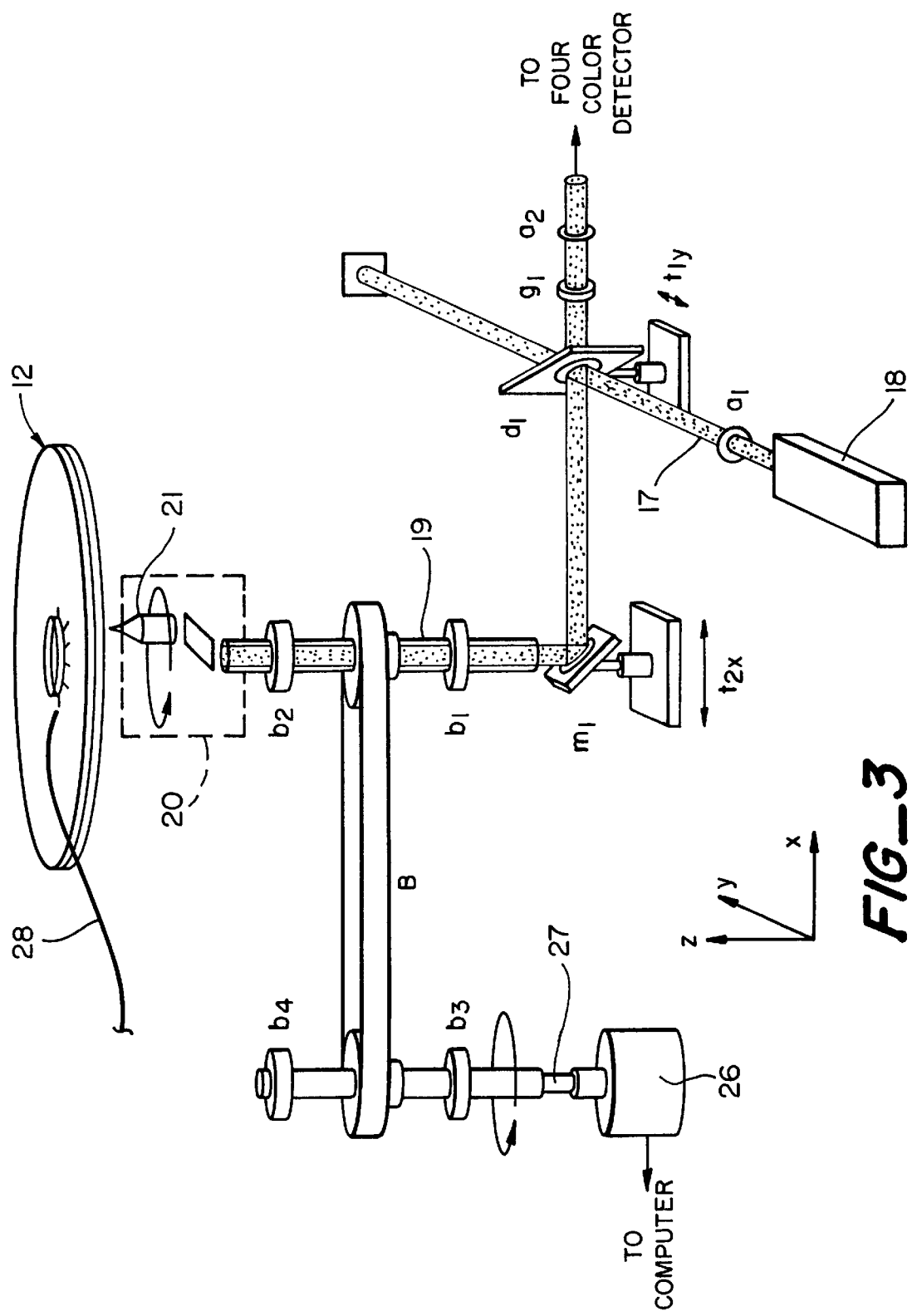
FIG_3

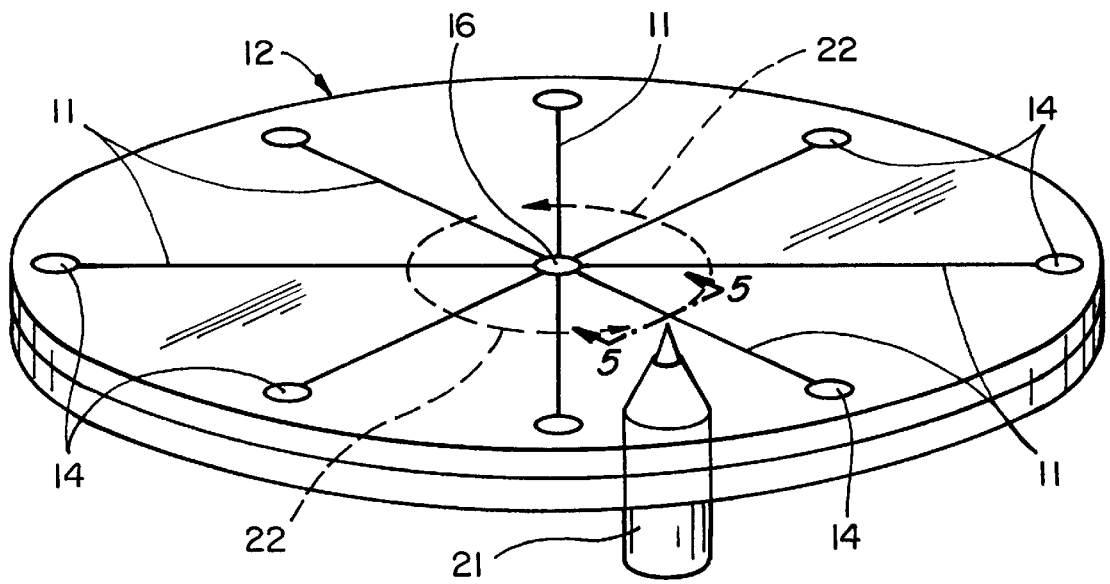
*FIG_4*
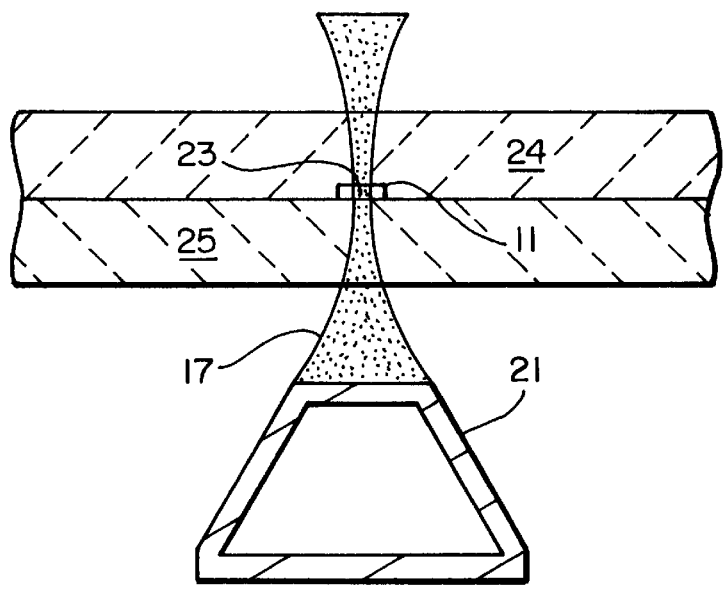
*FIG_5*

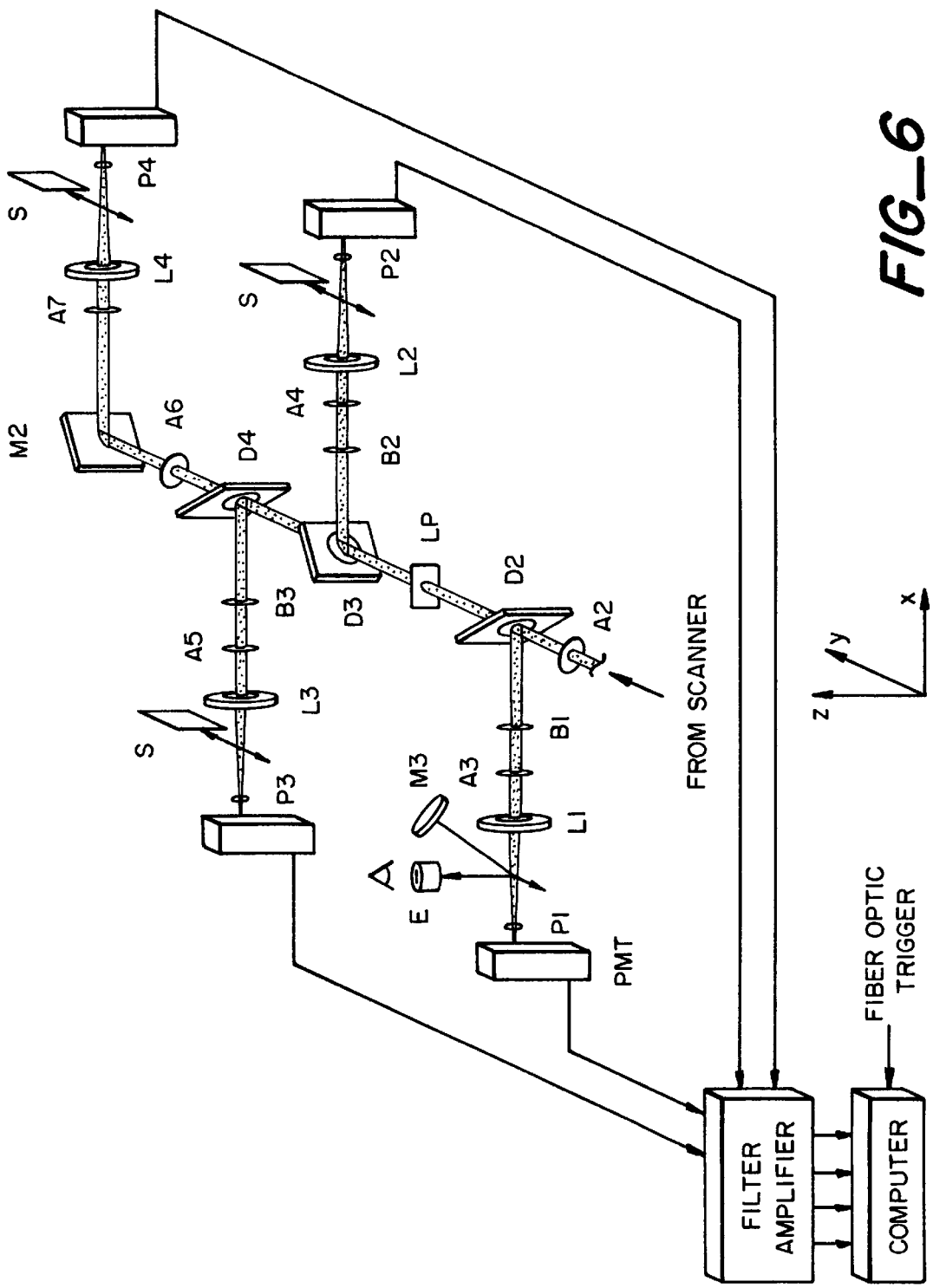
FIG_6

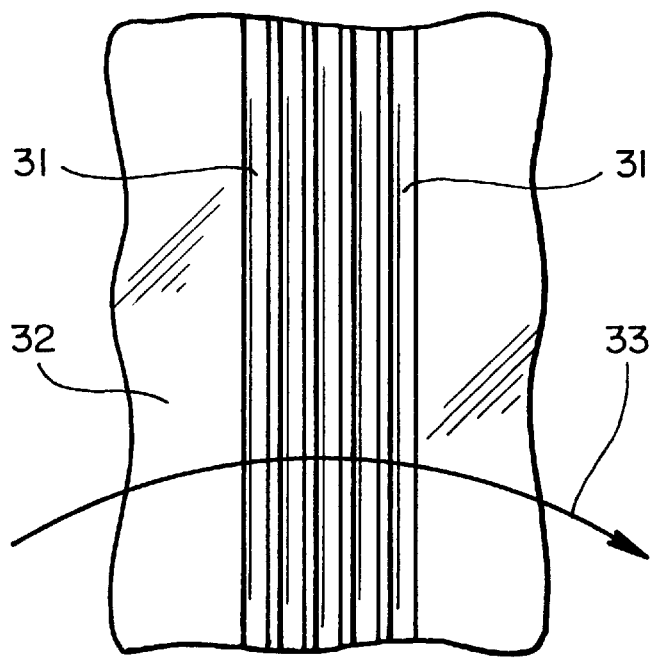
*FIG_7*
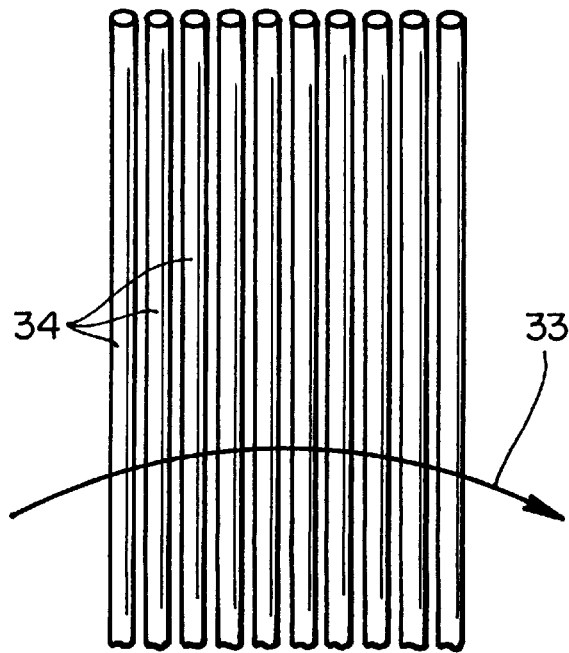
*FIG_8*

ROTARY CONFOCAL SCANNER FOR DETECTION OF CAPILLARY ARRAYS

BRIEF DESCRIPTION OF THE INVENTION

This invention relates generally to a capillary array scanner and more particularly to a capillary array confocal scanner for circularly scanning and detecting electrophoretic separations performed on planar capillary arrays.

BACKGROUND OF THE INVENTION

The goal of the Human Genome Project is to sequence the human genome which consists of $3 \times 10^9$ base pairs. Most automated DNA sequencers employ large slab gel configurations with multicolor fluorescence detection. The scanning confocal systems used in connection with detection of slab gels have also been useful in the detection of electrophoretic separations carried out in capillary arrays. Present state of the art confocal detection systems for capillary array electrophoresis have achieved sequencing rates of 25,000 bases/hr (96 samples, 500 bases/sample, 2 hrs/run). However, it is desirable to perform these separations even faster using optimized electrophoretic devices, at which point, detection of these separations becomes more challenging.

Methods for DNA fragment sizing and sequencing on photolithographically fabricated chips have been described in various published articles, for example: Woolley, A. T., and R. A. Mathies (1995), Ultra high speed DNA sequencing using capillary electrophoresis chips, *Anal. Chem.* 67:3676–3680; and Woolley, A. T., G. F. Sensabaugh, and R. A. Mathies (1997), High-Speed DNA Genotyping using Microfabricated Capillary Array Electrophoresis Chips, *Anal. Chem.* 69:2181–2186.

In the devices described in these publications, a glass substrate or chip is photolithographically etched to produce channels in the surface of the substrate. These channels are typically 10–50 micron in depth, 50–200 micron in width and can extend for 5–10 cm on the chip, depending on the layout. Then a second substrate is bonded on top of the etched surface to form enclosed channels or capillaries that are suitable for capillary electrophoresis separations. It has been shown that these microfabricated gel-filled channels can be used to perform high quality DNA separations that are 100-fold faster than slab gels and 10-fold faster than conventional capillary separations. It has also been shown that separations of dsDNA fragments, short tandem repeats, DNA sequencing fragments, proteins, amino acids and other chemical analytes can be performed on these chips. In these studies, single channels have been used and the detection has employed laser excited fluorescence detection of fragments in the single channel using conventional confocal or non-confocal microscope configurations.

Multiple channels have been fabricated on a chip and detected by illuminating and imaging the entire chip with a CCD detector, L. B. Koutny, D. Schmalzing, T. A. Taylor & M. Fuchs, Microchip Electrophoretic Immunoassay for Serum Cortisol, *Anal. Chem.* 68, 18–22 (1996). However, the sensitivity in the latter study was low. It is hard to see how this design can be used to detect large numbers of multiple channels at high speed.

Recently, chips have been fabricated with up to 12 channels (Wooley et al. (1997)). The anode ends of the channels are bundled together for detection and then the bundled channels were detected with a mechanical scan stage that moves the chip past a confocal detector. The linear scanning confocal detection system obtained fluorescence data at a 2 Hz rate. While this method works well to produce high sensitivity detection of multiple channels, it is difficult to see how this approach can be extended to more than 12 channels as the mechanical scanning of the chip past the detector is awkward and the scan rate (limited to 2 Hz) is not fast enough for most fragment sizing and sequencing applications.

The electrophoresis time for DNA sequencing on chips is very short (<10 min.) and consequently the chips must be scanned at rates of at least 10 Hz to provide adequate resolution of the bands. Linear scanners are not suitable for use at high scan rates because of the stresses placed on the motor systems during the stop and reverse phases of the scanning process and because of the time required for reversal.

The advantage of a confocal scanning system is its high numerical aperture, leading to high light collection efficiency, and its ability to limit the light detection to within the fluorescing confocal volume. This dramatically reduces the sensitivity of the system to stray light and also optically sections the capillary chip so as to reject stray light, fluorescence and scatter from the glass or plastic substrate.

In copending application Ser. No. 08/965,738 filed Nov. 7, 1997 incorporated herein by reference, there is described a microfabricated capillary array electrophoresis device or chip. The device includes an array of separation channels formed on a plate with an array of sample reservoirs coupled to the separation channels for introduction of samples into the channels. In one embodiment of the microfabricated capillary array electrophoresis device the channels extend radially or spirally outward from the center of the plate to the sample reservoirs to form a planar array. In another embodiment the planar array comprises a plurality of parallel microfabricated capillaries or channels. There is a need to provide a scanner that can perform high-sensitivity detection of separations on a radial array of capillary separation channels, or on a large array of linearly parallel channels, at a high sampling rate.

OBJECTS AND SUMMARY OF THE INVENTION

It is a general object of the present invention to provide a confocal scanning system which samples planar arrays of capillaries at a high rate.

It is another object of the present invention to provide a chip design in which the electrophoresis lanes (capillaries) are arranged to center radially at a central anode and a rotary confocal scanner for scanning the lanes in a circular motion.

It is another object of the present invention to provide an apparatus for scanning a radial array of capillaries to detect separations of substances in said capillaries.

It is a further object of the present invention to provide an apparatus for high sensitivity confocal detection of planar arrays of capillary separations at a high sampling rate.

These and other objects of the present invention are achieved by a rotary confocal scanner for detecting separations in a planar array of capillaries sequentially and repetitively during an electrophoresis separation.

BRIEF DESCRIPTION OF THE DRAWINGS

The foregoing and other objects of the invention will be more easily understood from the following description when read in connection with the accompanying drawings wherein:

FIG. 1 shows a radial capillary array electrophoresis chip for performing multiple channel electrophoretic analyses.

FIG. 2 shows spiral capillary array electrophoresis chip for performing multiple channel electrophoretic analyses.

FIG. 3 is a schematic diagram of the mechanical and optical parts of a rotary confocal scanner in accordance with the present invention.

FIG. 4 is a schematic view of the electrophoresis chip, the focused laser beam, and of the circular path interrogated by the scanner.

FIG. 5 is an enlarged view taken along line 5—5 of FIG. 4 showing the confocal volume that is illuminated and detected.

FIG. 6 is a schematic diagram of the four-color detector portion of the rotary scanner detection system.

FIG. 7 shows a microfabricated planar parallel array of capillaries scanned by a rotary scanner.

FIG. 8 shows a planar array of conventional capillaries scanned by a rotary scanner.

DESCRIPTION OF PREFERRED EMBODIMENT

FIGS. 1 and 2 show two multichannel capillary array electrophoresis chips where the capillary channels 11 are arranged radially and spirally on a circular glass sandwich structure 12. In these devices, the analyte is injected into the channels 11 from reservoirs 13 arranged on the perimeter of the micro-plate and analyzed through electrophoresis or other separation method by moving the analyte toward the central reservoir through a separation medium disposed in the channels 11. The analyte is moved by applying a voltage between the cathode 14 and central anode 16. The lanes are detected just before entry to the central anode 16. Linear and parallel as well as radial and spiral capillary array chips are described in detail in copending application Ser. No. 08/965, 738 filed Nov. 7, 1997, which is incorporated herein by reference in its entirety.

In accordance with the present invention, the detection of the separation in the capillaries is done with a novel confocal scanner that scans the lanes in a circular motion. In the preferred embodiment to be described hereinafter in detail, the chip is most easily scanned from below with a rotating scanner to leave the top of the chip available for access to the solution reservoirs 13, electrode contacts, etc. However, while this is convenient, the chip could also be scanned from above using mechanical or galvanometric scanners exploiting the same design principles.

FIG. 3–6 schematically show the mechanical and optical parts of a rotary scanner in accordance with the present invention. Referring to FIG. 3, an unpolarized or circularly polarized laser beam 17 passes from laser 18 through a defining aperture $a_1$, and is diverted by a dichroic beam splitter $d_1$, on translation stage $t_{1y}$, to a mirror $m_1$, mounted with orthogonal adjustments on translation stage $t_{2x}$. The mirror $m_1$ sends the beam up through a hollow shaft 19 supported by two high precision bearings $b_1$ and $b_2$. At the top of the shaft, a housing 20, not shown in detail, contains a rhomboid prism which displaces the beam by a given amount, for example 10 mm, sending it up through a microscope objective 21 (NA 0.5, working distance 1.7 mm, used in infinite conjugate mode), and into the plane of channels 11 in the chip. Means not shown can move the objective in small increments along the z direction thereby placing the focal point of the laser in the center of all the channels. FIG. 4 shows the laser beam focused on a channel 11 by the objective 21. The dotted circle 22 shows the circular scanning path. The enlarged view of FIG. 5 shows the laser beam 17 focused in the volume 23 of the capillary or channel 11 disposed between the plates 24 and 25.

A precision drive belt B drives the objective 21 through belt pulleys fixed between high precision bearings $b_1$ and $b_2$, and bearings $b_3$ and $b_4$. The solid shaft going through bearings $b_3$ and $b_4$ is connected to microstepping motor 26 through a flexible coupling 27. An optical fiber 28 is positioned in the path of the moving laser beam above the chip. Light from the rotating objective enters the optical fiber and is channeled to a photodiode which triggers the start of data acquisition.

Light from the sample volume, for example fluorescing DNA fragments, is collected by the objective 21, sent in a reverse path through the dichroic beam splitter $d_1$. It then passes through a plane parallel thick glass piece $g_1$ in a gimbal mounting to translate the beam to the center of the aperture $a_2$ which leads into a 4 color detector assembly (FIG. 6). Dichroic beam splitter $D_2$ (FIG. 6) reflects light at wavelengths 497–548 nm and the bandpass filter $B_1$ limits the wavelength range to 510–540 nm. Iris $A_3$ and the location of pinhole $P_1$, are used to define the unfocused beam path and appropriate dichroic position. An achromat lens $L_1$, provided with xyz adjustment, focuses the color-filtered beam onto the 200 μm confocal pinhole $P_1$. A diagonal mirror, $M_3$, which can be moved into the beam path between $L_1$ and $P_1$, creates an image plane at the top cover of the compartment, and a 20X Ramsden eyepiece E (Rolyn Optics) is used to view the image plane. Light passing through the pinhole, $P_1$, is detected by a photomultiplier tube.

The beam that passes through $D_2$ enters the second compartment, which is a mirror image of the first detection compartment. A removable longpass glass filter LP is used for additional blocking of the laser wavelength. Each successive compartment measures a longer wavelength range defined by the respective bandpass filters. Compartments 2, 3 and 4 each have a sliding shutter, S, in place of a diagonal mirror to block light from entering the photomultipliers. Compartment 4 contains a mirror in place of a dichroic beam splitter and no bandpass filter is used to limit the long wavelength detection range. Plasma lines in the primary laser beam are significant beyond 590 nm and are removed using a line filter. The outputs of the photomultiplier tubes (PMTs) are amplified and filtered using 500 Hz low-pass filters. The signal is digitized using a 16-bit ADC operating at 1 KHz. The intensity data are collected bidirectionally and stored in a PC. The act of focusing the detected fluorescent light on the pinholes affects confocal detection. This means that the emission is collected from just the confocal volume that is illuminated by the laser within the channel or capillary in the chip.

In one example, 96 electrophoresis lanes converged at the central anode well 16 whose radius was <1cm. The radius of the beam path produced by the rotary scanner was $r_a$ (~1 cm), and its path length was 62.832 mm for r=1 cm. Leaving space for a fiber optic to initiate data acquisition, there was about 640 μm between lane centers. This divides into electrophoresis lanes and space between lanes. Taking data every 20 μm, we would have 3072 data points per revolution. The 32 data intervals which make up the 640 μm data spacing can be divided up into data from the channels and data from the spaces between channels. At 10 revolutions (RPS), the data rate would be 30.72 kHz or 32.55 μs/data pt. The outputs of the amplifier/lowpass filters are simultaneously sampled by four independent analog to digital converters (ADCs). The ADCs are controlled by a multi-tasking program which samples all positions, strips away non-channel data, averages and logs the data to a computer. Channel spacing and data rate are variable and can be changed easily in the multitasking program.

It is apparent that the rotary scanner can be used to scan any planar arrays of capillaries. FIG. 7 schematically shows use of the rotary scanner to scan a planar parallel array of microfabricated capillaries 31 formed on glass substrate 32 along the line 33. FIG. 8 shows use of the rotary scanner to scan a plurality of capillaries 34 such as described in U.S. Pat. No. 5,274,240 arranged in a parallel planar relationship.

This invention does not depend on the configuration of the lanes in the microchip and can be easily used in conjunction with any configuration that uses a circular detection path. A confocal fluorescence galvanometric scanner could equivalently be used to effect circular or elliptical scanning of these chips. The advantage of the rotary confocal scanner of the present invention is that it permits very high sampling rates (10 Hz or more), confocal detection and simultaneous four or more color detection of the fluorescent signals.

What is claimed is:

1. A scanner for exciting and detecting energy from an excitation volume in a capillary passage and providing an output representing the material in the excitation volume comprising:

a plurality of side-by-side capillary passages disposed in a plane, a source of radiant energy, an optical means including an objective lens for receiving the radiant energy and focusing said radiant energy in the excitation volume, means for continuously and repetitively moving said objective lens in a circular pattern to scan an excitation volume in each sequential capillary passage, said objective lens collecting radiant energy from said excitation volume in each sequential capillary passage and directing the radiant energy into a confocal optical system, a detector positioned to receive the radiant energy from said confocal optical system and provide an output signal, and a computer means for receiving said output signal and providing an output representative of the material in said sample volume.

2. A scanner as in claim 1 including means for detecting the position of a scanned volume and providing it to the computer to correlate the output with the capillary being scanned.

3. A scanner as in claims 1 or 2 in which the confocal system includes a spatial filter and a spectral filter.

4. A scanner as in claim 1 or 2 in which the capillaries are radially oriented in a plane.

5. A scanner as in claim 1 or 2 in which the capillaries are oriented parallel to one another in a plane.

6. A scanner as in claim 4 in which said radially oriented capillaries spiral outwardly.

7. A scanner for exciting and detecting radiation from an excitation volume in each of a plurality of capillary passages and providing an output representing the material in the excitation volume comprising:

a plurality of side-by-side capillary passages disposed in a plane, a source of radiant energy of a first wavelength, an optical means including an objective lens for receiving and focusing said radiant energy in an excitation volume in the plane of said plurality of side-by-side capillary passages, means for moving said objective lens in a circular pattern so that said excitation volume sequentially and repetitively is within one of said plurality of side-by-side capillary passages to excite material in one said passage and cause the material to radiate energy at a plurality of different wavelengths, said objective lens serving to collect the radiated energy of said different wavelengths and direct it to an optical system including, a plurality of dichroic beam splitters for selectively directing the radiated energy of each of said plurality of different wavelengths to a different location, a plurality of sets of spatial and spectral filter means one for each of said different wavelengths, and a plurality of detection means, one for each set of spatial and spectral filter means, for receiving the radiated energy of each different wavelength and providing corresponding output signals, and computer means for receiving and processing said signals to provide an output representative of the material in the excitation volume in each of said plurality of side-by-side capillary passages.

8. A scanner as in claim 7 in which the capillaries are radially oriented.

9. A scanner as in claim 8 in which said radially oriented capillaries spiral outwardly.

10. A scanner as in claim 7 in which the capillaries are parallel to one another in said plane.

* * * * *